United States Patent
Zhu et al.

(10) Patent No.: US 11,723,530 B2
(45) Date of Patent: Aug. 15, 2023

(54) METHOD AND APPARATUS FOR PERFORMING A VISUAL FIELD TEST

(71) Applicant: UCL Business LTD, London (GB)

(72) Inventors: Haogang Zhu, London (GB); David Garway-Heath, London (GB); David Crabb, London (GB); Marco Miranda, London (GB)

(73) Assignee: UCL BUSINESS LTD, London (GB)

( * ) Notice: Subject to any disclaimer, the term of this patent is extended or adjusted under 35 U.S.C. 154(b) by 1218 days.

(21) Appl. No.: 16/322,052

(22) PCT Filed: Aug. 10, 2017

(86) PCT No.: PCT/GB2017/052358
§ 371 (c)(1),
(2) Date: Jan. 30, 2019

(87) PCT Pub. No.: WO2018/033705
PCT Pub. Date: Feb. 22, 2018

(65) Prior Publication Data
US 2020/0178789 A1    Jun. 11, 2020

(30) Foreign Application Priority Data
Aug. 15, 2016  (GB) .................................. 1613923

(51) Int. Cl.
*A61B 3/024* (2006.01)
*A61B 3/00* (2006.01)
*A61B 3/06* (2006.01)

(52) U.S. Cl.
CPC ............ *A61B 3/024* (2013.01); *A61B 3/0008* (2013.01); *A61B 3/0025* (2013.01);
(Continued)

(58) Field of Classification Search
CPC ..... A61B 3/024; A61B 3/0008; A61B 3/0025; A61B 3/0033; A61B 3/0041; A61B 3/063
See application file for complete search history.

(56) References Cited

U.S. PATENT DOCUMENTS 4,818,091 A * 4/1989 Sadun .................. G02C 7/12
351/49
5,050,983 A * 9/1991 Johnson ................ A61B 3/024
351/224

(Continued)

FOREIGN PATENT DOCUMENTS

EP    2361547 A1    8/2011
EP    2984983 A1    2/2016

(Continued)

OTHER PUBLICATIONS

Fitzke, F. W. et al., "Peripheral displacement thresholds in normals, ocular hypertensives and glaucoma," Perimetry Update 1986/1987, E. Greve and A. Heijl, Editors, Kugler & Ghedini: The Hague, The Netherlands. 447-452.

(Continued)

*Primary Examiner* — William R Alexander
*Assistant Examiner* — Sharrief I Broome
(74) *Attorney, Agent, or Firm* — Hamilton, Brook, Smith & Reynolds, P.C.

(57) ABSTRACT

A method and apparatus are provided for measuring a sensitivity level across a visual field of a subject defined by a set of locations. The method comprises: presenting a sequence of visual stimuli on a display, wherein each stimulus in the sequence has a respective intensity level and is positioned on the display to correspond to a respective location from the set of locations; obtaining from the subject, for each stimulus, a respective binary response indicating whether or not the stimulus was seen by the subject; and after receiving the response from the subject for a given (Continued)

stimulus in the sequence, using a statistical model to estimate, for each location in the set of locations, the sensitivity level at that location; wherein the statistical model incorporates information about correlations in responses between different locations from the set of locations and takes as input, the respective binary response, intensity level and location for multiple stimuli presented in said sequence up to and including the given stimulus.

23 Claims, 9 Drawing Sheets

(52) U.S. Cl.
CPC .......... *A61B 3/0033* (2013.01); *A61B 3/0041* (2013.01); *A61B 3/063* (2013.01)

(56) References Cited

U.S. PATENT DOCUMENTS

| | | | |
|---|---|---|---|
| 2010/0249532 A1* | 9/2010 | Maddess | A61B 3/024 600/300 |
| 2013/0201452 A1* | 8/2013 | Crabb | A61B 3/024 351/224 |
| 2016/0220162 A1* | 8/2016 | Mantysalo | A61B 5/7445 |
| 2020/0178789 A1* | 6/2020 | Zhu | A61B 3/0041 |

FOREIGN PATENT DOCUMENTS

| | | | | |
|---|---|---|---|---|
| EP | 2984983 B1 * | 9/2020 | ........... | A61B 3/0025 |
| WO | 0040140 A1 | 7/2000 | | |
| WO | 0230291 A1 | 4/2002 | | |
| WO | 2011138587 A3 | 11/2011 | | |
| WO | WO-2011138587 A2 * | 11/2011 | ............ | A61B 3/024 |

OTHER PUBLICATIONS

Garway-Heath, D. F. et al., "Scaling the hill of vision: the physiological relationship between light sensitivity and ganglion cell numbers," Invest Ophthalmol Vis Sci., 41(7): 1774-82 (2000).

King-Smith, et al., "Efficient and Unbiased Modifications of the QUEST Threshold Method: Theory, Simulations, Experimental Evaluation and Practical Implementation," Vision Res., 34: 885-912 (1994).

Verdon-Roe, G. M., et al., "Optimum Number of stimulus oscillations for motion displacement detection in glaucoma," Kugler Publications: The Hague, The Netherlands pp. 97-102, (2000).

Verdon Roe, G. M., "Development of a multi-location motion displacement test for detection of early glaucoma," Doctoral Thesis, Institute of Ophthalmology, University College London (2006).

Verdon-Roe, G. M., "Exploration of the psychophysics of a motion displacement hyperacuity stimulus," Invest Ophthalmol Vis Sci., 47(11): 4847-55, (2006).

Search Report of the GB Intellectual Property Office for Application No. GB1613923.0 dated Feb. 10, 2017.

International Search Report of PCT Application No. PCT/GB2017/052358, dated Nov. 6, 2017.

Written Opinion of PCT Application No. PCT/GB2017/052358, dated Nov. 6, 2017.

International Preliminary Report on Patentability of PCT Application No. PCT/GB2017/052358, dated Feb. 28, 2019.

* cited by examiner

METHOD AND APPARATUS FOR PERFORMING A VISUAL FIELD TEST

FIELD

The present invention relates to an apparatus and method for performing a visual field test, for example, to identify or investigate glaucoma.

BACKGROUND

There are various known techniques for measuring or detecting a loss of sensitivity across a visual field, see for example: WO 2011/138587 and U.S. Pat. No. 5,050,983. One known form of test is a supra-threshold test, which measures whether or not a subject exceeds a predetermined threshold for loss of sensitivity at various locations across the field of view (the predetermined threshold used may vary from one location to another). Such a supra-threshold test may be used (for example) for screening, in that individuals who exceed the predetermined threshold are suspected of having visual field damage, and can therefore be provided with further testing. This is to be contrasted with a threshold test, which measures the limit of sensitivity for a given subject at various locations across the field of view. Thus the outcome of a supra-threshold test is a spatial distribution (map) of binary values (pass/fail) indicating whether the sensitivity is above or below the threshold at each location, whereas the outcome of a threshold test is a spatial distribution (map) of numerical values corresponding to the threshold of visual sensitivity at each location.

One facility for performing such a threshold or supra-threshold test is the Moorfields Motion Displacement Test (MDT) which has been developed by a collaboration between Moorfields Eye Hospital, London, the UCL Institute of Ophthalmology and City University London, see Fitzke et al 1987, Verdon-Roe et al 2006a and Verdon-Roe et al 2006b. The Moorfields MDT involves the presentation of a pattern of multiple vertical lines. The lines are scaled in size by an estimate of retinal ganglion cell density, see Garway-Heath et al 2000, except for centrally placed lines, which are sized to be resistant to the effects of optical blur so that the test can be performed without refractive (spectacle) correction, see Verdon-Roe 2006a.

During the Moorfields MDT, the viewer is asked to maintain their gaze on a specific (fixation) target for the duration of the test. The lines are subjected one at a time to a brief period of horizontal oscillation at a frequency of approximately 5 Hz, see Verdon-Roe et al 2000. Each period of line oscillation presents a stimulus to the visual field. The viewer is asked to indicate whenever they detect such a stimulus. The overall test comprises a sequence of such line presentations (stimuli), where each location is activated in turn, generally in accordance with some randomised order (so the user cannot predict the location of the next stimulus), and the user provides feedback for each stimulus that they observe.

One use for a motion displacement test is as a threshold test to measure the visual sensitivity of a subject across the field of vision. For example, the movement (amplitude of oscillation) of the stimulus can be made smaller and smaller until a threshold is reached beyond which the movement is no longer discernible to the subject. Such sensitivity measurements can be used both for detecting the presence of disease or other damage to the visual field, and/or for measuring the progression (deterioration) of such disease/damage.

A motion displacement test may also be used as a supra-threshold test. FIG. 1A is a schematic illustration of the results of a supra-threshold test from the Moorfields MDT for a spatial pattern of 52 locations to match the Humphrey 24-2 visual field test pattern of standard automated perimetry (SAP). The small circles indicate locations where the user successfully responded to the stimulus at that location, while the crosses indicate locations at which the viewer did not respond to the stimulus. The duration of the test is approximately 90 seconds to allow for a stimulus to be presented once at each test location. It has been found in practice that the response of a viewer is not completely reliable (repeatable). In particular, in some procedures there is approximately a 5% chance that a healthy observer will accidentally miss any given stimulus. For a test sequence comprising 52 locations (and one presentation per location), this presents an expected rate of 2.6 false negative responses per test sequence (where a response is regarded as false negative if it incorrectly fails to be seen).

Accordingly, it is known in supra-threshold vision tests to have a retest strategy, whereby the overall test sequence includes repetitions of the stimulus for at least some locations. FIG. 1B illustrates one such retest strategy, which involves repeating the stimulus once for each test location i.e. each location has a first presentation and a second presentation (usually not consecutively, but rather interspersed with stimuli at other locations). If the first presentation and the second presentation both give the same result (either both positive or both negative), this result is then accepted as correct for that location. On the other hand, if the first and second presentations give different results, then a third presentation is performed for this location. This leads to three presentations at the relevant location, and the final outcome is taken on a majority basis.

The approach of FIG. 1B is referred to as a supra-threshold 2/3 test, in that it measures whether a subject can or cannot see the stimulus on a majority 2 out of 3 basis. In contrast, the approach of FIG. 1A is referred to as a supra-threshold 1/1 test, because the conclusion is based on the findings of just a single measurement. It will be appreciated that the retest strategy of FIG. 1B involves testing each location at least twice more particularly, usually about 10% of the locations are tested three times, while the remaining locations are tested twice. The number of false negatives with this approach is much lower than compared with the approach of FIG. 1A (reduced by a factor of about 10), so that the results are more reliable. However, having to provide repeat stimuli at a given location increases the duration of the overall test (by a factor of just over two, if scaling by the number of activations).

Similar issues arise in performing threshold tests. These are often performed by using a "staircase" approach, in which the intensity of a stimulus is reduced step-by-step until it is no longer visible. FIG. 2A illustrates the results from such a threshold test (sometimes referred to as a test trail), in which the open circles represent stimulus presentations. The y-axis indicates the user response, which is a binary outcome, with 1 indicating that the user saw the stimulus presentation, and 0 indicating that the user did not see the stimulus presentation. The intensity of the stimulus is indicated by the x-axis scale of sensitivity (in dB), whereby higher values of sensitivity denote lower values of intensity (since greater sensitivity is needed to see a weaker presentation). Note that the intensity of a stimulus may represent its brightness, but could also indicate some other parameter that impacts visibility—for example, in the case of the Moorfields MDT, the intensity corresponds to the amplitude of displacement of a given line.

The test trail shown in FIG. 2A depicts an ideal outcome, whereby a user sees all presentations down to (and including) a sensitivity of 24, and does not see any presentations at a sensitivity of 26 or lower. If we plot a line through the test results, as indicated by line 6, this line has 3 regions: a first region 2A where we are generally sure the user can sees the presentation; a second region 2B where we are generally sure that the user does not see the presentation; and a third, intermediate, region 2C, which is shown in FIG. 2A as a straight line interpolation between regions 2A and 2B. We see that the intermediate region 2C represents a sharp transition (a steep drop) from the seen presentations to the unseen presentations. This sharp transition allows us to make an accurate estimation of the sensitivity threshold of the user at this location to be 25±1, as denoted by marker 3 in FIG. 2A.

In practice however, the presentation results for a particular user might be more complex, such as for the test trail shown in FIG. 2B. Here, the user responses are again indicated by open circles, with a value of 1 for seen and 0 for unseen. As illustrated in FIG. 2B, the user sees all the presentations up to and including a sensitivity of 18, does not see the presentation at a sensitivity 20, sees the presentations at a sensitivity of 22 and 24, does not see the presentation at a sensitivity of 26, does see the presentations at a sensitivity of 28 and 30, and does not see any of the presentations at a sensitivity of 32 and above.

As with FIG. 2A, we can plot a line 16 through the presentation results. This line again has 3 regions: a first region 12A where we are generally sure the user can sees the presentation; a second region 12B where we are generally sure that the user does not see the presentation; and a third, intermediate, region 12C, which is again represented as a straight line interpolation between regions 12A and 12B.

Note that the slope of the intermediate region 12C in FIG. 2B is much shallower than the steep slope of the intermediate region 2C in FIG. 2A. This indicates a much greater level of uncertainty as to the actual threshold of sensitivity for this user. In particular, the transition of FIG. 2B is much less sharp than the transition of FIG. 2A, and hence our estimation of the sensitivity threshold of the user at this location might be 26±5, as denoted by marker 13 in FIG. 2B. Accordingly, the uncertainty associated with the sensitivity threshold from FIG. 2B is much greater than in the ideal case of FIG. 2A.

As described above for FIGS. 1A and 1B, we can improve the accuracy of supra-threshold sensitivity measurements by repeating presentations. This general approach of repeating presentations can also be applied in order to reduce the uncertainty of threshold measurements. However, extending the duration of a test (whether threshold or supra-threshold) by repeating presentations raises the practical costs of administering the test, since for a given set of equipment and medical support staff, the number of subjects that can be tested in a given time period is reduced.

A further issue is that if the duration of a test is prolonged, the subject of the test may tire, and this in itself may lead to inconsistencies as to which presentations are seen or not seen. As a practical example, a typical visual field test may have 54 test locations, each of which has a contrast sensitivity threshold between 0 dB and 50 dB. The visual field test tries to find the threshold at each of these locations by issuing stimuli at various contrasts and collecting responses from a human subject. A test only on the integer sensitivities forms a large ($51^{54}$) search space, but the number of queries should not exceed 400 because fatigue may start to significantly affect the performance of the subject if the test takes a long time (perhaps more than say 5-10 minutes). It is therefore desirable to be able to reduce the time taken for administering a vision test such as the Moorfields MDT while still maintaining a desired level of statistical accuracy for the test results.

SUMMARY

The invention is defined in the appended independent claims.

In one aspect, a method and apparatus are provided for measuring a sensitivity level across a visual field of a subject defined by a set of locations. The method comprises: presenting a sequence of visual stimuli on a display, wherein each stimulus in the sequence has a respective intensity level and is positioned on the display to correspond to a respective location from the set of locations; obtaining from the subject, for each stimulus, a respective binary response indicating whether or not the stimulus was seen by the subject; and after receiving the response from the subject for a given stimulus in the sequence, using a statistical model to estimate, for each location in the set of locations, the sensitivity level at that location. The statistical model incorporates information about correlations in responses between different locations from the set of locations and takes as input, the respective binary response, intensity level and location for multiple stimuli presented in said sequence up to and including the given stimulus.

In a second aspect, a method and apparatus are provided for measuring a sensitivity level across a visual field of a subject defined by a set of locations. The method comprises presenting by a control system a sequence of visual stimuli on a display, wherein each stimulus in the sequence has a respective intensity level and is positioned on the display to correspond to a particular location from the set of locations; obtaining from the subject by a control system via an input mechanism, for each stimulus, a respective binary response indicating whether or not the stimulus was seen by the subject; and after receiving the response from the subject for a given stimulus in the sequence, using a statistical model in the control system to estimate, the sensitivity level at that location. The statistical model takes as input the respective intensity levels and responses for the stimuli presented in said sequence up to and including the given stimulus and uses a Bayesian approach to estimate the sensitivity level at that location by finding a sensitivity level that maximises the likelihood of the responses for the stimuli presented in said sequence.

The first and second aspects can share various preferred implementations as appropriate, as set out in the dependent claims.

BRIEF DESCRIPTION OF THE DRAWINGS

FIGS. 2A and 2B illustrate two test trails from a threshold test, with FIG. 2A showing an ideal situation in which fully consistent responses are received, while FIG. 2B shows an example in which more inconsistent responses are received.

DETAILED DESCRIPTION

Many existing current threshold test algorithms summarise a currently estimated threshold using a set of parameters, while disregarding the actual responses from the subject in respect of previous stimuli. A subsequent stimulus is then planned according to the current threshold estimates, based on the set of parameters. As more responses are collected, the threshold parameters are updated accordingly. However, subjects may produce errors during the test, so that the estimate of threshold may be misled by such erroneous responses, thereby leading to suboptimal planning of the test strategy. In contrast, the approach described utilises many (typically all) previous responses directly for determining the current estimated threshold (rather than just using the most recent response to update the set of parameters determined from previous responses). This has been found to provide quicker and more robust testing of visual sensitivity. More particularly, the approach described herein proposes a visual test based on a trail traced threshold test (T4) approach which is able to make use of all previous stimuli and the corresponding response trail from the subject when estimating the threshold level and planning the test strategy.

Formalisation

Figure 1A:
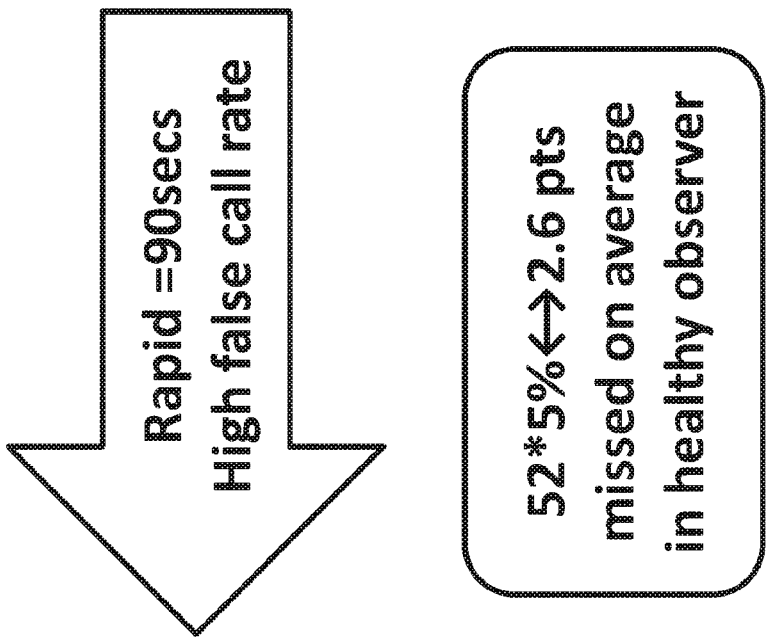
FIGS. 1A and 1B are schematic illustrations of two known retest strategies used in a supra-threshold visual field test for detecting visual field damage.
Figure 1A:
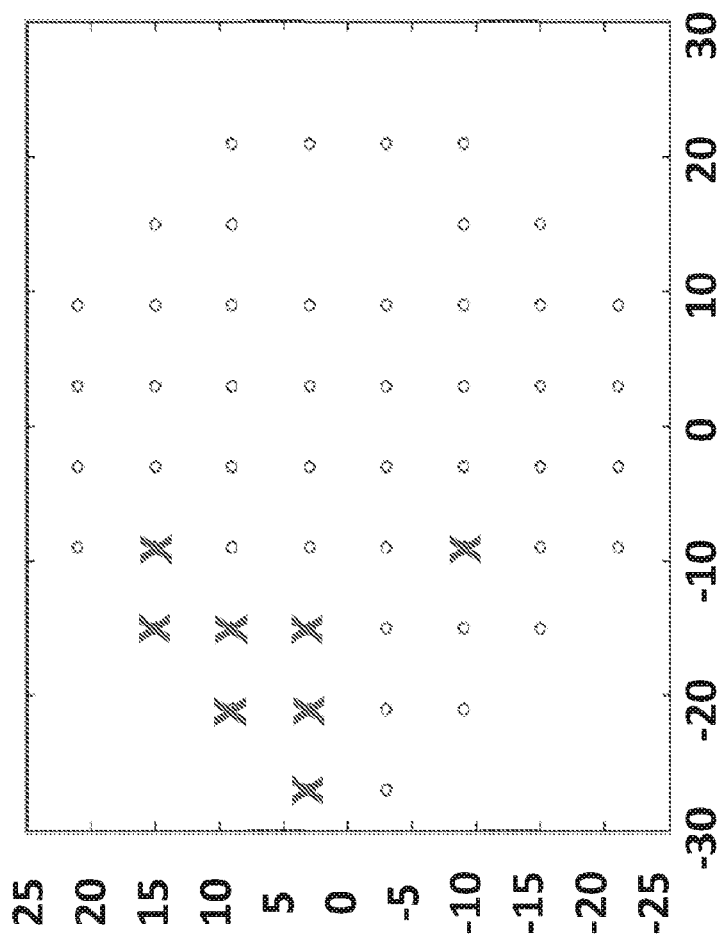

In the T4 approach, we assume that a test is carried out at a set of M locations $\{x_m\}_{m=1}^{M}$ where $x_m$ is a vector of coordinates for each of the test locations, such as illustrated, for example, in FIG. 1A (for ease of representation, location $x_m$ is sometimes referred to herein as location m). During the test, a series of queries are issued sequentially by presenting for each query a defined stimulus to the subject at one location. The response of whether the stimulus (presentation) is perceived (seen) or not perceived (not seen) is recorded. Formally, the ith query stimulus at intensity level $s_i \in \mathbb{R}$ is presented at location $x_{n_i}$ ($n_i \in \{1: M\}$) and the response from the subject is $r_i \in \{0, 1\}$, where $r_i=1$ indicates a positive (seen) response and $r_i=0$ indicates a negative (unseen) response. (Note that as defined herein, $s_i$ and $r_i$ represent the single sequence of stimuli and corresponding responses presented to and received from the user across the set all M locations).

We assume that the response at each location $x_m$ is generated from a target function $h_m(s): \mathbb{R} \to \{0, 1\}$ defined on a stimulus level s and the response is contaminated by noise. For most types of tests, the target function $h_m$ can be defined as a simple thresholding function:

$$h_m(s \mid t_m) = \begin{cases} 1 & \text{if } s \leq t_m \\ 0 & \text{if } s > t_m \end{cases} \quad \text{(Eq. 1)}$$

where $t_m$ represents the threshold level at location m (and is the parameter being measured by the vision test).

It is assumed that the probability of the noisy response is parametrically defined for each location and is governed by a set of parameters $\theta_m$:

$$f_m(s) := p(r=1 \mid s, \theta_m) \quad \text{(Eq. 2)}$$

In other words, $f_m(s)$ represents the probability of having a positive response (r=1) at a given sensitivity level s and for a given set of parameters $\theta_m$ (which reflect the noise level). Note the explicit dependency on $\theta_m$ in $f_m(s)$ is now dropped for notational convenience.

With the target function $h_m$ defined in Equation 1, the T4 approach searches for the threshold $t_m$ at each location $x_m$ such that the uncertainty of having a positive or negative response is maximised, i.e. the probability of having a positive or negative response to a stimulus at the level of $t_m$ equals to 0.5, hence $f_m(t_m)=0.5$; in other words, a positive response and a negative response are equally likely (and so must have a probability of 0.5, since these are the only two possibilities). In general, we assume that $f_m(s)$ is differentiable with respect to s.

The T4 strategy includes the following main functionalities. Firstly, the test procedure proposes the next query (stimulus presentation), including the level of the stimulus, and the location at which the stimulus will be presented. Secondly, the parameters $\theta_m$ in $f_m(s)$ are learned (or otherwise accommodated) according to the responses received from the user in response to each query that is presented. Thirdly, the test procedure is completed when the termination criteria are met, including a reliable estimation of the user sensitivity threshold at each location ($t_m$ at each location $x_m$). The T4 approach tries to reduce the number of queries so that the test terminates in a shorter period of time than existing approaches.

The T4 strategy described herein provides a generalised binary search which is able to accommodate noise in the received responses, and adopts a Bayesian sequential update for the response probabilities after each response is received. Such a search procedure helps to ensure convergence assuming the learning rate is larger than the noise level. In general, the T4 test strategy described herein: 1) plans the test, and each stimulus presentation in turn, based on the whole trail (history) of responses for this test; and 2) incorporates spatial correlation when a response trail from multiple locations is available. The T4 method described herein is well-suited for performing a time-sensitive test (so as to avoid user fatigue), in which only a relatively small number of queries are utilised compared with a much larger multi-location searching space.

We now describe in more detail one particular implementation of the T4 method, in which it is assumed that $f_m(s)$ can be represented as follows:

$$f_m(s) = p(r_i = 1 \mid s_i, \mu_m \sigma_m) = \frac{1}{2}\left[1 - \text{erf}\left(\frac{s_i - \mu_m}{\sigma_m \sqrt{2}}\right)\right] \quad \text{(Eq. 3)}$$

where:

$\mu_m$ represents the current estimate of the threshold ($t_m$), and
$\sigma_m$ represents the uncertainty (standard deviation) associated with this estimate;
$s_i$ represents the stimulus level of the ith presentation;
$r_i$ represents the response (0 or 1) to the ith presentation; and
erf is the error function given by:

$$\text{erf}(y) = \frac{1}{\sqrt{\pi}} \int_{-y}^{y} e^{-u^2} du$$

and is 0 for y=0, and goes to 1 as y goes to infinity (and −1 as y goes to minus infinity). Accordingly, if $\sigma_m \to 0$, then the probability of getting a positive response ($r_i$=1) goes to 1 if $\mu_m$ is greater than the sensitivity $s_i$, and goes to 0 if $\mu_m$ is less than the sensitivity $s_i$. It will be appreciated that this is exactly what would happen in the absence of noise. (Note that the approach of Equation 3 does not formally model the noise parameters $\theta_m$, rather the noise is implicitly accommodated by the distribution $\sigma_m$ of $\mu_m$).

Given N stimuli $s = \{s_i\}_{i=1}^{N}$ and corresponding responses $r = \{r_i\}_{i=1}^{N}$ from a subject, the test described herein tries to find the best fit of $\mu_m$ and $\sigma_m$ in order to estimate the true threshold ($t_m$) plus the uncertainty associated with this threshold (for all values of m). As the test progresses, the current values of $\mu_m$ and $\sigma_m$ (for all values of m) are also used to determine the next stimulus to be presented to the user.

Spatial Correlation

The spatial correlation between a location $x_p$ and a location $x_q \in \{x_m\}_{m=1}^{M}$ is quantified as:

$$w_{pq} = \begin{cases} e^{-\frac{1}{2}\left(\frac{\text{dist}_{pq}^2}{\sigma_d^2} + \frac{\angle_{pq}^2}{\sigma_\angle^2}\right)} & \text{if } p \text{ and } q \text{ are in the same hemifield} \\ 0 & \text{otherwise} \end{cases} \quad \text{(Eq. 4)}$$

where:

$\text{dist}_{pq}$ is the Euclidian distance between the locations $x_p$ and $x_q$ in the visual field (whereby increasing $\text{dist}_{pq}$ decreases the spatial correlation);

$\angle_{pq}$ is the difference between the angles at which the respective optic nerve fibres passing through locations $x_p$ and $x_q$ enter the optic nerve head (whereby increasing $\angle_{pq}$ decreases the spatial correlation, while $\angle_{pq}$ is zero if locations $x_p$ and $x_q$ lie on the path of the same optic nerve);

$\sigma_d$ and $\sigma_\angle$ are scale parameters. For the standard Humphrey Field Analyzer (HFA) 24-2 test pattern the scale parameters are chosen to be $\sigma_d$=6° and $\sigma_\angle$=14°. More specifically, $\sigma_d$=6° is the angular distance between two neighbouring locations $x_p$ and $x_q$ in the visual field and $\sigma_\angle$=14° is the reported 95% confidence interval of population variability in the nerve fibre entrance angle into the optic nerve head.

Note that in Equation 4, if the two locations $x_p$ and $x_q$ lie in different hemifields of the visual field due to the physiological distribution of optic nerve fibres, then the correlation $w_{pq}$ is automatically set to 0. Overall, the spatial correlation $w_{pq} \in (0, 1]$ and a larger value of $w_{pq}$ implies a stronger correlation between locations $x_p$ and $x_q$. According to Equation 4, $w_{pq}$=1 if and only if p=q, i.e. locations $x_p$ and $x_q$ are the same, otherwise $w_{pq}$<1.

Figure 1B:
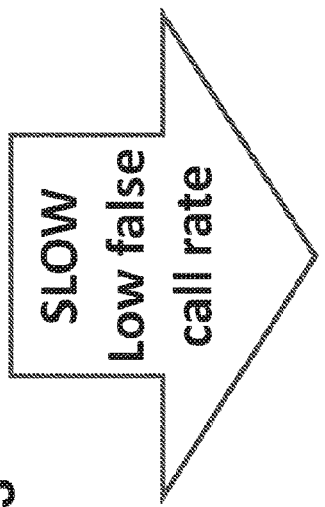
Figure 1B:
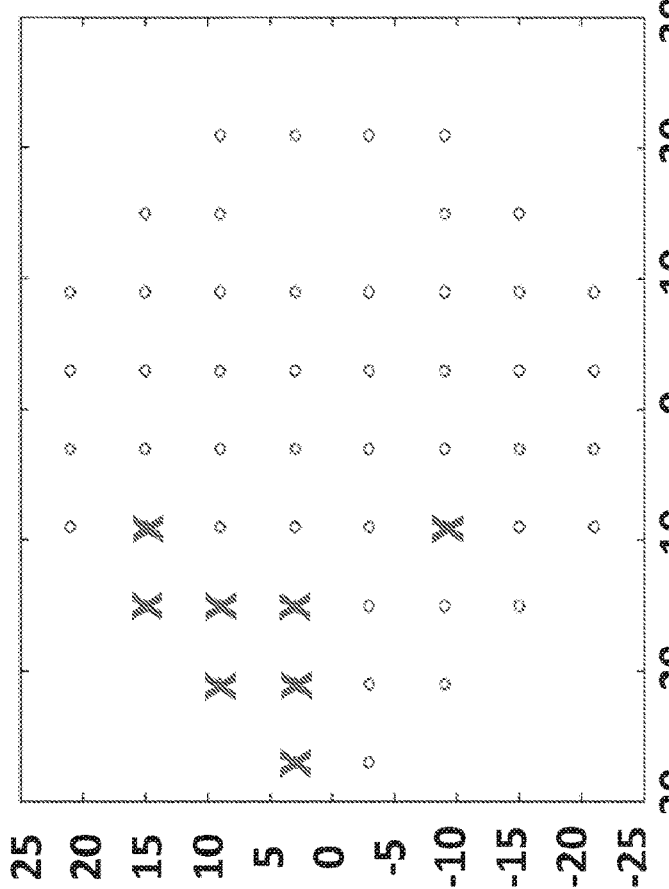
Figure 3:
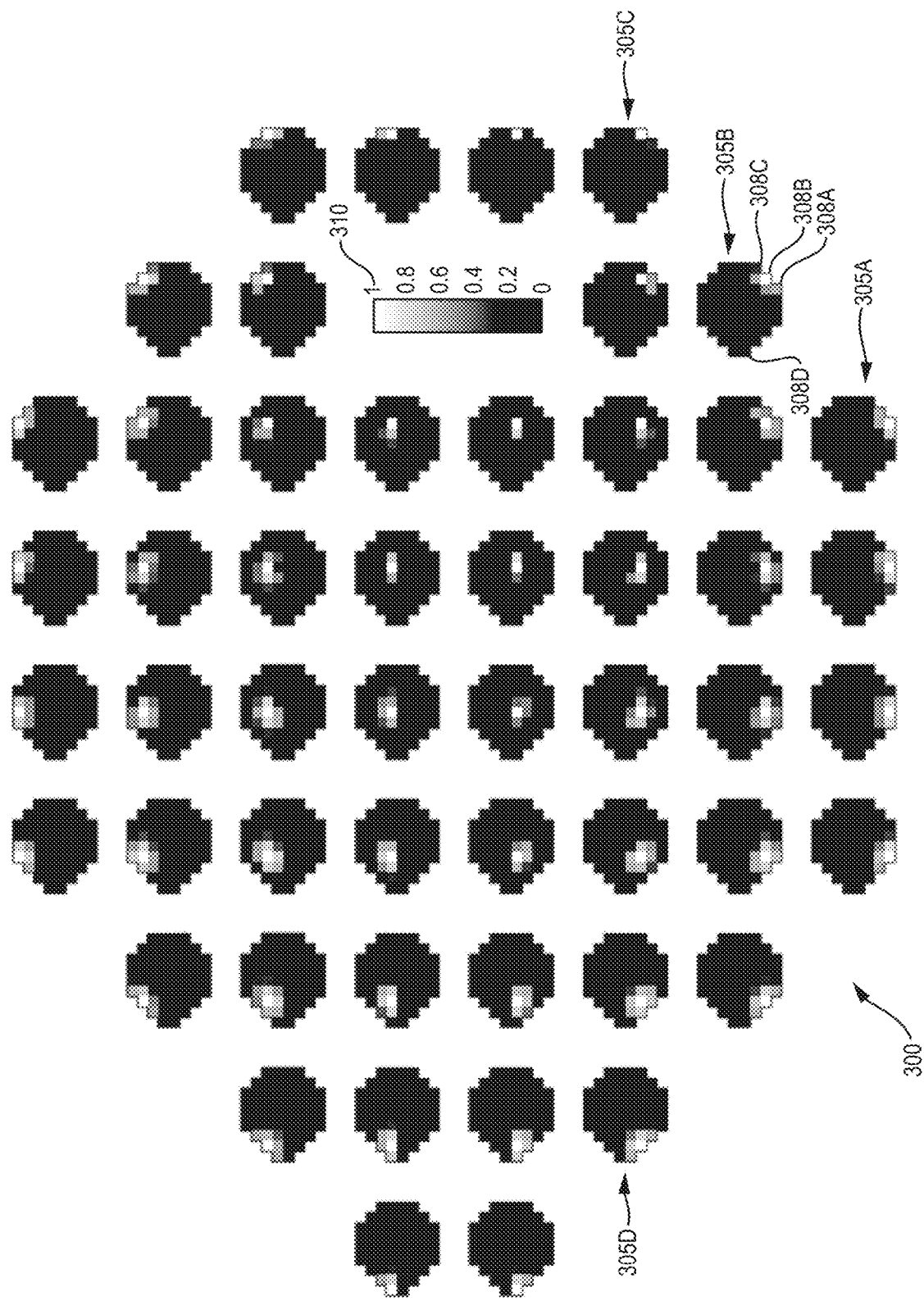
FIG. 3 is a schematic representation showing correlations between different locations in the visual field.

FIG. 3 is a schematic illustration of the value of the correlation $w_{pq}$ across a visual field of view 300. The field of view is defined by a pattern of 52 test locations 305A, 305B, 305C, 305D . . . (this is the same pattern as utilised in FIGS. 1A and 1B. The correlation $w_{pq}$ therefore denotes a correlation between two such test locations 305, denoted as p and q. At each test location 305 is a greyscale plot that comprises 52 pixels one pixel corresponding to each respective test location 305. The 52 pixels with a greyscale plot share the same spatial arrangement as that of the corresponding test locations 305 within the visual field 300.

Each pixel shows the value of the correlation $w_{pq}$ where location p is determined by the location of the greyscale plot within the overall visual field 300, and the location q is determined by the location of the relevant pixel within the individual greyscale plot. The actual value of the correlation $w_{pq}$ is indicated by the greyscale shading of the pixel, in accordance with the scale 310. In particular, a white pixel indicates a correlation of 1 (and hence by implication p=q), while a black pixel indicates a correlation of 0. Intermediate values of the correlation are represented by shades of grey, with darker shades representing lower correlations. It can be seen from FIG. 3 that test locations tend to be correlated (value>0) with neighbouring (physically adjacent) locations, but there is no correlation (value of 0—indicated by black) with more distant or remote locations.

For example, with reference to test location 305B, the greyscale plot for this test location has four individual pixels indicated. Pixel 308B corresponds in position to the position of test location 305B within visual field 300—i.e. this represents the correlation of test location 305B with itself ($w_{pp}$), and hence is white to indicate a correlation value of 1. Pixel 308D corresponds in position within the greyscale plot to the position of test location 305D within visual field 300, so pixel 308D represents the correlation between test location 305B and test location 305D. Pixel 308D is black to indicate a correlation value of zero between test location 305B and test location 305D—as would be expected because these two locations are widely separated across the visual field 300. Pixel 308A represents the correlation between test locations 305B and 305A, since the position of pixel 308A within the plot for location 305B corresponds to the position of test location 305A within field 300. Similarly, pixel 308C represents the correlation between test locations 305B and 305C, since the position of pixel 308C within the plot for location 305B corresponds to the position of test location 305C within field 300. Both pixels 308A and 308C have a grey shading, indicating an intermediate correlation with location 305B. Again, this would be expected since test locations 305A and 305C are immediate neighbours of test location 305B. Since pixel 308A is a somewhat lighter grey than pixel 308C, this indicates that the correlation between test locations 305A and 305B is greater than the correlation between test locations 305C and 305B.

The correlations shown in FIG. 3 can be found experimentally, determined theoretically (based on knowledge of the configuration of optical nerves), or generated from a combination of the two. They may, for example, be held numerically in a look-up table, without any indication of the underlying biological factors (as opposed to the formulation of Equation 4). In general, it can be seen from FIG. 3 that test locations are generally correlated with their neighbouring locations, but not with more remote (widely separated) test locations. On the other hand, it is also apparent from FIG. 3 that a test location is not necessarily correlated with all of its immediate neighbours.

Returning to Equation 3, this defines the probability of a positive response for a stimulus at location m based on distribution information ($\mu_m$ and $\sigma_m$) specific to location m. However, with the definition of the spatial correlation presented above in Equation 4, we can obtain additional information about $f_m(s)$ from information (responses) at neighbouring locations $n_i \neq m$. Thus for a given distribution at location $x_m$, the likelihood of the ith response at location $x_1$ is defined as a binomial distribution weighted by the spatial correlation $w_{mn_i}$ between the two locations:

$$p(r_i \mid s_i, w_{mn_i}, \mu_m, \sigma_m) = \frac{f_m(s_i)^{w_{mn_i} r_i}(1 - f_m(s_i))^{w_{mn_i}(1-r_i)}}{f_m(s_i)^{w_{mn_i}} + (1 - f_m(s_i))^{w_{mn_i}}} \quad \text{(Eq. 5)}$$

(Note that Equation 5 is derived from a binomial probability density function for a binary response; it would also be possible, although potentially more complicated, to directly model the distribution using other distributions for seen presentations obtained theoretically and/or experimentally from psychophysics, visual studies, etc.).

Since $r_i$ is just a binary value, $r_i \in \{0, 1\}$, where $r_i=1$ indicates a positive (seen) response and $r_i=0$ indicates a negative (unseen) response, we can simplify Equation 5 as follows:

$$p(r_i = 0 \mid s_i, w_{mn_i}, \mu_m, \sigma_m) = \frac{(1 - f_m(s_i))^{w_{mn_i}}}{f_m(s_i)^{w_{mn_i}} + (1 - f_m(s_i))^{w_{mn_i}}} \quad \text{(Eq. 5A)}$$

$$p(r_i = 1 \mid s_i, w_{mn_i}, \mu_m, \sigma_m) = \frac{f_m(s_i)^{w_{mn_i}}}{f_m(s_i)^{w_{mn_i}} + (1 - f_m(s_i))^{w_{mn_i}}} \quad \text{(Eq. 5B)}$$

It can be seen easily from Equations 5A and 5B that the two probabilities for $r_i=0$ and $r_i=1$ sum to unity (as one would expect). Note also that if $w_{mn_i}=0$, i.e. there is no correlation in the responses between location $x_m$ and location $x_{n_i}$, then according to Equations 5A and 5B, $$p(r_i=0 \mid s_i, w_{mn_i}, \mu_m, \sigma_m) = P(r_i=1 \mid s_i, w_{mn_i}, \mu_m, \sigma_m) = 0.5$$

In other words, for zero correlation the distribution at location $x_m$ is not giving us any useful predictive information about the likely outcome at location $x_{n_i}$ (rather just a basic 50/50 split); conversely, if $w_{mn_i}=1$, which in practical terms implies that locations $x_m$ and $x_{n_i}$ are the same (m=n), then Equations 5A and 5B reduce to the following binomial distribution (identical to Equation 3 above for location $x_m$):

$$p(r_i = 1 \mid s_i, w_{mn_i}, \mu_m, \sigma_m) = f_m(s_i)^{w_{mn_i}}$$

$$p(r_i = 0 \mid s_i, w_{mn_i}, \mu_m, \sigma_m) = 1 - f_m(s_i)^{w_{mn_i}}$$

It will be appreciated that intermediate values of the correlation, $w_{mn_i}$, between 0 and 1, result in probabilities which are intermediate between: (i) a 0.5/0.5 split, and (ii) the probabilities at location $x_m$.

Figure 2A:
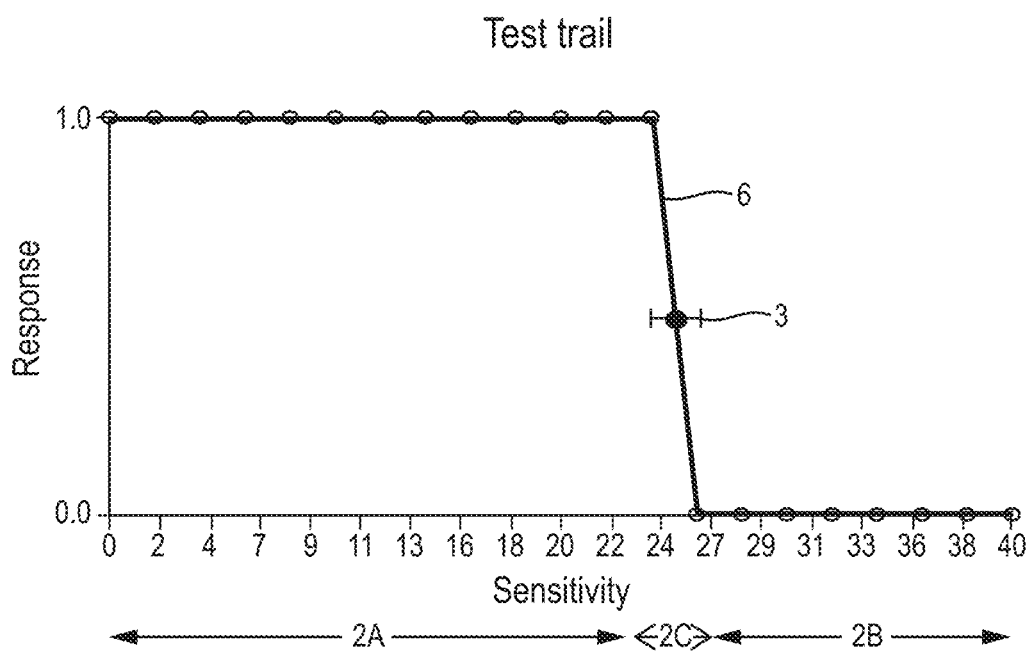
Figure 2B:
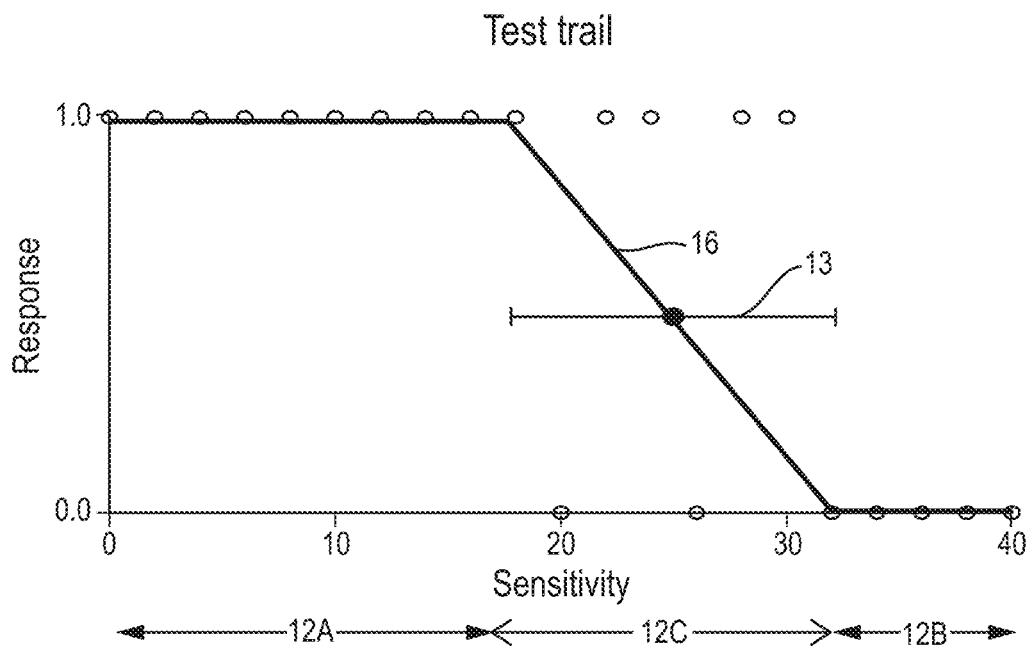
Figure 3A:
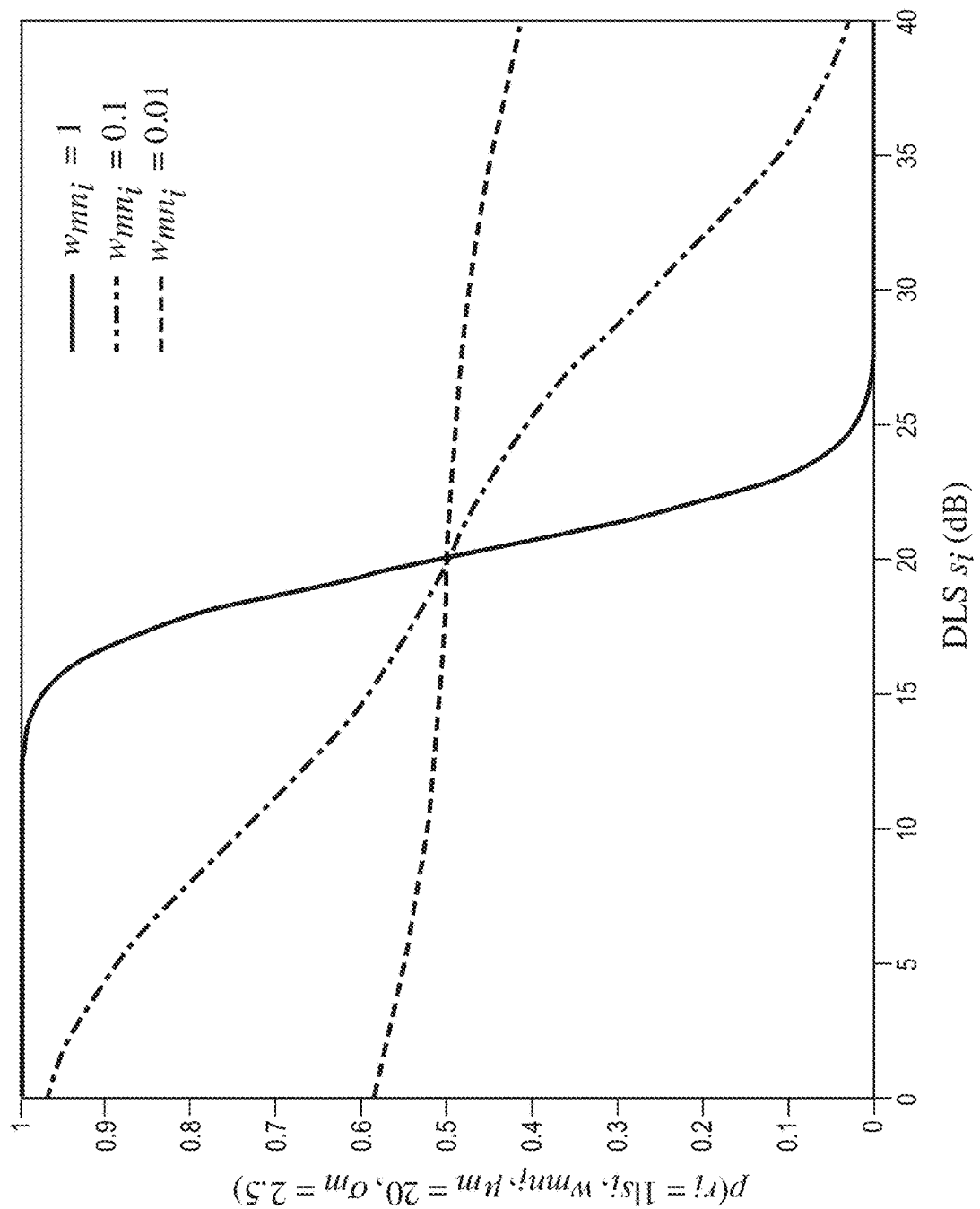
FIG. 3A is a plot showing how a probability for a positive response at a first location can be estimated based on the estimated threshold sensitivity distribution at a second location in combination with knowledge of the correlation between the first and second locations.

FIG. 3A is a plot of probability of a seen response ($r_i=1$) as a function of sensitivity (in dB) according to Equation 5 for three different values of correlation $w_{mn_i}$ (and is therefore comparable to the plots of FIGS. 2A and 2B). In particular, FIG. 3A illustrates examples of a weighted binomial distribution for a positive (seen) response at location $n_i$, given the known (estimated) distribution at location m (as defined by $\mu_m=20$ and $\sigma_m=2.5$). The solid line in FIG. 3A has $w_{mn_i}=1$, which implies m=n$_i$, in which case the plot directly represents the distribution corresponding to the assumed values of $\mu_m=20$ and $\sigma_m=2.5$.

However, as $w_{mn_i}$ drops below one, so by implication m≠n$_i$, we are using our knowledge of the distribution at location m to predict a probability distribution (as a function of intensity) for a positive outcome at location n$_i$. In particular, FIG. 3A shows plots for $w_{mn_i}=0.1$ (dot-dashed line) and $w_{mn_i}=0.01$ (dashed line). Both of these distributions for $w_{mn_i}<1$ are still centered on an intensity of 20 (corresponding to the value of $\mu_m=20$), but have a spread or uncertainty ($\sigma>2.5$) which increases with falling correlation. Overall, it can be seen from FIG. 3A that lowering the correlation $w_{mn_i}$ in effect drags the probability values towards the midpoint (0.5) so that the distribution has a shallower (less steep) profile, with the lower correlations exerting a stronger pull than the higher correlations to flatten the distribution. This flattening results in the transition of the probability distribution from 1 down to 0 being distributed (extended) over a wider range of intensities, which in turn makes it more difficult to predict the response to a given stimulus level.

If we use the distribution at location $x_m$ to predict the response at location $x_{n_i}$, the uncertainty of the prediction, such as shown in FIG. 3A, generally increases when location $x_{n_i}$ is further away from location $x_m$. If location $x_{n_i}$ is sufficiently far away from location $x_m$ that the correlation (or lack of it) approaches 0 ($w_{mn_i} \to 0$), Equation 5 becomes a flat line at 0.5, indicating the largest uncertainty about the estimated threshold level at response location $x_{n_i}$. On the other hand, for locations $x_{n_i}$ having values of correlation $w_{mn_i}>0$, we are able to augment our knowledge of location $x_{n_i}$ using knowledge of previous responses not only from location $x_n$ but also from other (typically neighbouring) locations $x_m$. In other words, although FIG. 3A illustrates the probability distribution for a positive response at location $x_{n_i}$ based on knowledge of the distribution at just a single location $x_m$, we can combine information from all locations (m=1 . . . M, including m=n$_i$) (or at least from all locations that have a non-zero correlation with location n) to make a more refined estimate of the probability distribution for a positive response at location $x_{n_i}$.

Inference of Threshold and Uncertainty

In the T4 strategy, a Bayesian approach is utilised for estimating threshold sensitivity. Accordingly, we define a suitable prior probability for $\mu_m$ and $\sigma_m$ (as defined in respect of Equation 3), with both being represented by a normal distribution:

$$p(\mu_m)=N(\mu_\mu,\sigma_\mu); p(\sigma_m)=N(\mu_\sigma,\sigma_\sigma) \quad \text{(Eq. 6)}$$

For $\mu_m$, the mean ($\mu_\mu$) and standard deviation ($\sigma_\mu$) of this normal distribution are set as non-informative: $\mu_\mu=20$ dB and $\sigma_\mu=1000$ dB. It will be appreciated that $\mu_\mu$ represents a typical mid-sensitivity level for a threshold test trail such as shown in FIGS. 2A and 2B, which span a range of approximately 0 dB through to 40 dB, although the range of these plots is much less than $\sigma_\mu=1000$ dB. Conversely, for $\sigma_m$, the mean ($\mu_\sigma$) and standard deviation ($\sigma_\sigma$) of this normal distribution are set as informative: $\mu_\sigma=10$ dB and $\sigma_\sigma=20$ dB. It will be appreciated that these values reflect the overall scale of FIGS. 2A and 2B in terms of measuring threshold sensitivity, and hence approximate the initial uncertainty in the estimate of threshold sensitivity. Furthermore, the prior distributions for $\mu_m$ and $\sigma_m$ defined above may be refined or replaced as appropriate using other information (if available), for example, the result from previous testing of a subject (or a population of subjects), etc.

The posterior probability for $\mu_m$ and $\sigma_m$ can be determined by multiplying Equations 3 and 4 above for all N stimuli $s=\{s_i\}_{i=1}^N$, together with their respective responses $r=\{r_i\}_{i=1}^N$, and spatial correlations $w=\{w_i\}_{i=1}^N$, leading to the following expression:

$$p(\mu_m,\sigma_m \mid r,s,w) \propto \Pi_{i=1}^N p(r_i \mid s_i,w_{mn_i},\mu_m,\sigma_m) p(\mu_m) p(\sigma_m) \quad \text{(Eq. 7)}$$

By way of explanation, we note that $\mu_m$ and $\sigma_m$ together determine $f_m$ (as per Equation 3), and we can simplify Equation 7 by dropping the explicit dependency on s and w, which are known in advance, to give, for a single observation (the ith in the sequence): $p(f \mid r) \propto p(r \mid f) p(f)$, which follows the standard Bayesian formula. Accordingly, the inference of the threshold $\mu_m$ and its uncertainty $\sigma_m$ can be performed by maximising the log of Equation 7, subject to the constraint that for a conventional perimetry test, we know that 0 db$\leq\mu_m\leq$40 dB, such as shown in FIGS. 2A and 2B. This maximisation can be performed using a trust-region algorithm (or any other appropriate algorithm for such a maximisation).

Equation 7 allows the estimated distribution $f_m$ for any location m to be updated after each presentation of a stimulus (and associated response), irrespective of whether this presentation occurred at location m itself, or at a different location n ($\neq$m). Consequently, after each presentation and response, the maximisation of Equation 7 can be performed for every location (m=1 ... M) in order to update the distribution of $f_m$ for that location. The estimated distribution for a given location is therefore derived by making direct use of all previous observations (responses), including:

(i) all previous responses at the given location (m); and
(ii) all previous responses at locations (n) other than the given location (i.e. n$\neq$m) (although responses at locations n for which $w_{mn}$=0 may be excluded, since these do not contribute to our knowledge regarding the given location, as per Equation 7).

Note that for both (i) and (ii), it is the actual responses (i.e. the binary values $r_i$=0 or 1) that are used directly for updating the estimated distribution $f_m$. This is to be contrasted with some existing techniques, which first calculate a threshold sensitivity at each location based on the responses from that respective location, and then perform a smoothing of the threshold sensitivities across the field of view. In this latter approach, responses at location n only contribute indirectly to estimating the threshold sensitivity at location m, in that the responses at location n are first used to determine the threshold sensitivity at location n, and it is this threshold sensitivity (but not the previous responses themselves) at location n that is then utilised to help estimate the threshold sensitivity at location m. By using all previous responses in this manner, it will be appreciated that maximum amount of information is retained and exploited in the threshold sensitivity determination.

Overall Test Procedure

As described above in relation to FIGS. 2A and 2B, some known systems perform this determination in a relatively simple manner by selecting a given location, and then presenting a sequence of stimuli at that given location, with a steady decrease in intensity level, until at least one (more typically, several) stimuli are not seen for the given location, and then moving on to repeat this staircase for another location.

Figure 4:
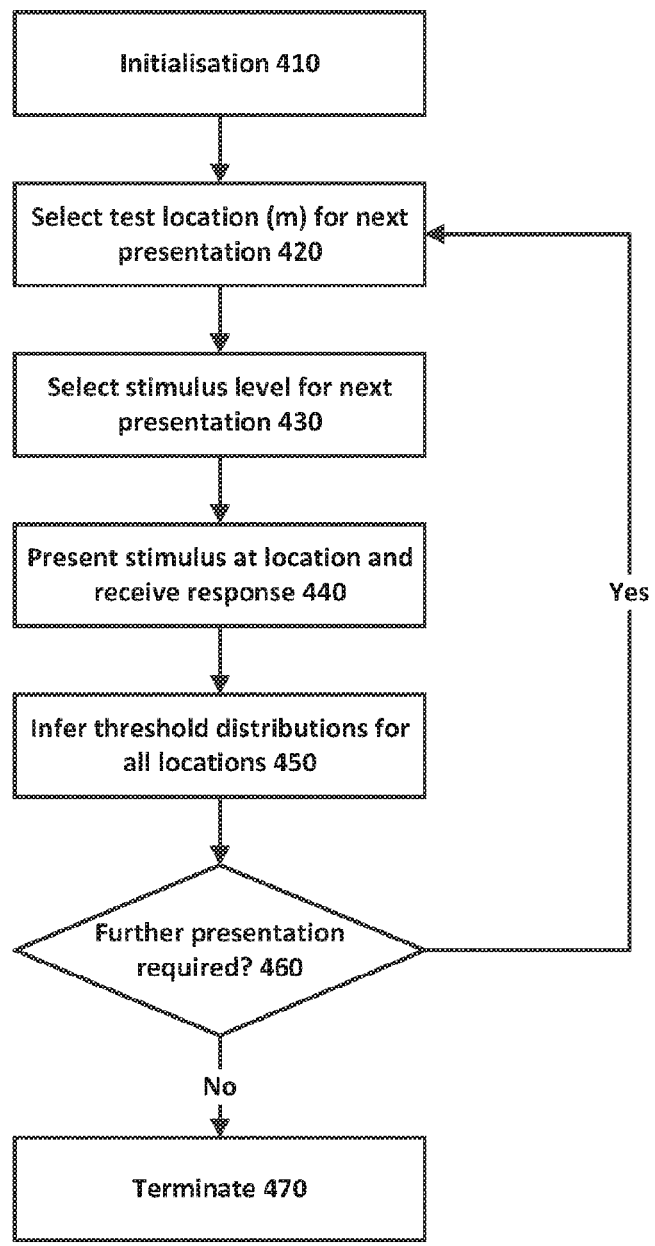
FIG. 4 is a flowchart illustrating an example test strategy for performing a visual test as described herein.

The T4 test strategy, such as illustrated in the flowchart of FIG. 4, is significantly different from such a known strategy. The process commences at operation 410 with initialization. This includes initializing the parameters of Equation 3 in accordance with the prior distributions of Equation 6, namely the two normal distributions for $\mu_m$ and $\sigma_m$ having a suitable mean and variance.

Once the initialization has completed, the system now determines the test location for the next (first) presentation $x_{n_i}$ (operation 420). There are various ways in which this next test location may be selected or determined. For example, for the first presentation, this might typically be selected on a random basis, or according to some predetermined ordering, or possibly based on user input (e.g. if there is a particular region of the visual field of the subject being tested that is of greatest clinical interest).

Assuming that we choose a location m for the next presentation (i.e. m=$n_i$), we now select or determine an intensity level for this stimulus presentation (operation 430). This stimulus intensity is set to equal the mean of the estimate of the threshold for the location (i.e. $\mu_m$) (which for the very first presentation will reflect the selected prior distribution for $\mu_m$). The test strategy now proceeds to present the stimulus at the selected location and intensity level, and to receive the response from the subject—seen, or not seen (operation 440).

At operation 450, the test system now performs the maximisation of Equation 7 for all test locations (m=1 ... M) in order to infer the threshold distributions (mean and variance) for every test location. Note that this updating directly re-uses all previous user responses, which will generally have been obtained from presentations at a number of different locations, and determines the values of $\mu_m$ and $\sigma_m$ for each of the test locations (i.e. for m=1 ... M).

At operation 460, the test system determines whether another presentation is required. This decision may be made according to one or more criteria. For example, the test strategy may require a minimum of a certain number of presentations (e.g. 2, 3 or 4) at each test location and/or that the uncertainty $\sigma_m$ at each location (m) is below a certain threshold that represents the desired accuracy of the test (e.g. this may be comparable to the uncertainty 3 in FIG. 2A, rather than the uncertainty 13 in FIG. 2B). If no further presentations are required, the method terminates, with the values of $\mu_m$ and $\sigma_m$ obtained for each location at operation 450 becoming the final output.

On the other hand, if further presentations are required, we loop back to operation 420, and select the test location for the next presentation. Once at least one stimulus has been performed and the response acquired, the threshold distributions derived at operation 450 can be used to help select the test location for the next presentation. For example, the location having the highest uncertainty ($\sigma_m$) might be selected for the next presentation; if there are multiple locations all sharing the same highest uncertainty, then one of these might be selected at random. Another possible approach would be to look for a group of neighbouring locations which have a relatively high sum of their combined uncertainties, since a presentation at one of these location may help not only to reduce the uncertainty for the selected location, but also for its neighbouring locations. In practice, some test procedures may start by selecting test locations according to some predefined strategy, e.g. using a pseudo-random ordering, until each location has had a threshold number of presentations (e.g. 2, 3 or 4). Once this desired level of coverage has been achieved, the procedure may identify the (sub)set of locations for which the uncertainty ($\sigma_m$) is still above a given threshold. The next location is then selected at operation 420 from this (sub)set of locations, for example, on a random basis, or by selecting the test location having the highest uncertainty as determined from operation 450.

It will be appreciated that for each processing loop, the inference of operation 450 is effectively performed anew. In other words, parameters $\mu_\mu$, $\sigma_\mu$, $\mu_\sigma$ and $\sigma_\sigma$ retain their initial values, and $\mu_m$ and $\sigma_m$ are re-determined from scratch according to the maximisation of Equation 7—but this time including the information for the most recent presentation, i.e. location, intensity, and response, as well as the information for all the previous presentations. However, given that the maximisation of Equation 7 is performed algorithmically, the estimated values of $\mu_m$ and $\sigma_m$ from a prior iteration of operation 450 might be used, for example, as starting values in the maximisation procedure for operation 450 of the current iteration (in general this should not impact the outcome of the maximisation, in terms of the newly inferred values of $\mu_m$ and $\sigma_m$, but it may allow the maximisation to converge more quickly).

The processing loop of operations 420 through 460 is repeated until no further presentations are required, e.g. because the uncertainty ($\sigma_m$) for all locations m is below a predefined threshold, or because some other termination criterion has comes into effect, e.g. a limit on the total number of iterations or presentations. Note that the total number of iterations (and hence presentations) performed to obtain the desired set of measurements can be considered as an indicator of the duration of the test. As described above, a shorter duration not only allows a greater throughput of testing, but also helps to reduce the problem of subject fatigue (which may compromise the accuracy of the results).

It will be appreciated that FIG. 4 is presented by way of example only—a number of different implementations will follow the illustrated procedure, while other implementations may differ somewhat from the illustrated procedure. By way of example, some implementations may maintain a pool of candidate locations that need further testing in order to confirm the threshold. For example, this pool may comprise (i) locations that have not yet been tested K times (for example, K=2, 3 or 4), and/or locations for which the threshold uncertainty $\sigma_m$ is greater than some specified value—e.g. $\sigma_m$>1 dB for conventional perimetry testing (although any other suitable value could be used instead). The selection of the test location at operation 420 is then performed with respect to this pool of candidate locations (i.e. test locations that are not in this pool are not selected). On the first iteration of the processing shown in FIG. 4, the pool would typically contain all of the test locations in the visual field. The contents of the pool are then reviewed at operation 460, which can remove test locations from the pool if they now satisfy the criteria set out above (e.g. at least 3 tests and $\sigma_m \leq 1$ dB). If removing these test locations causes the pool to become empty, then no further presentations are required, and so we progress from operation 460 to the termination 470. On the other hand, if there is still at least one test location remaining in the pool, we return to operation 420 to perform the next iteration.

In some implementations, the maximisation of operation 450 to infer the threshold distribution for location m may discount stimuli presented at locations n that have a low or zero correlation with location m. For example, the maximisation for inferring the distribution at location m may discount stimuli presented at locations n if $w_{mn}$<0.1 (or some other suitable threshold), since these presentations contribute little (if anything) to the inference of the distribution at m, and discounting stimuli in this manner improves the computational efficiency.

It may also be appropriate to ignore some or all spatial correlations for other reasons (this could be achieved by setting the relevant correlation values $w_{mn}$ to zero). For example, if there was some (suspected) clinical condition that might cause a significant departure from the correlations set out in Equation 4, it might be desirable to determine the sensitivity of each location individually, just from presentations to that location (albeit this would generally take longer than if also using the spatial correlations).

In some implementations, the maximisation of operation 450 to infer the threshold distribution for location m may also (or alternatively) discount stimuli for other reasons. One approach, for example, would be to discard presentations that are relatively early in the sequence (low values of i)—this might be desirable to reduce processing overhead, because there would then be fewer presentations to incorporate into the maximisation of Equation 7. NB it generally makes more sense to retain the later rather than earlier presentations, because the intensity levels of these presentations are likely to be closer to the true sensitivity values of the respective locations, and hence the results from such presentations may be more informative.

Although the processing of FIG. 4 has been described primarily in the context of threshold testing, it may also be adapted for a supra-threshold test. For example, if a threshold level is set at TL for location m, then this location might be considered as passing (or failing) the threshold if the estimated sensitivity was above (or below) this threshold by a given number of standard deviations (e.g. 2, 2.5 or 3). For example, we might have: $(\mu_m - TL)/\sigma_m > 2.5$—positive outcome, and $(TL - \mu_m)/\sigma_m > 2.5$—negative outcome (otherwise undecided).

The skilled person will also appreciate that as well as many procedural modifications that could be made to the T4 procedure, there are also statistical modifications that could also be made. For example, in the above analysis, we have assumed a normal (and hence symmetric) distribution for $\mu_m$. This implies that (for example), if the true sensitivity level is 20 dB (as per the scaling of FIGS. 2A, 2B and 3A), then the probability of missing a presentation at 17 dB (3 dB brighter than the sensitivity level) is the same as the probability of seeing a presentation at 23 dB (3 dB below the sensitivity level). Although this is a reasonable approximation, the use of other distributions (or composite distributions) could accommodate asymmetry, and hence may have the potential to represent the actual physical properties of the eye. In general, the maximisation (optimisation) of Equation 7 could then be performed with respect to whatever parameters are used to represent this distribution.

Similarly, as discussed above, observational noise is implicitly incorporated into Equation 3 by virtue of $\sigma_m$, however, in other implementations, the observational noise may be explicitly incorporated as for Equation 1. In this case, the sensitivity level for a given location would not be a variable per se, but rather a parameter ($t_m$). The optimisation would then infer the value of $t_m$ for each location so as to maximise the likelihood of noise arising from the distribution $\theta_m$ that would produce the given observations (responses), based on the sensitivity levels of the presentations and the spatial correlation values of Equation 4. In this approach, the uncertainty of the estimated sensitivity would be based on the width of the maximum of the noise likelihood according to the inferred value of $t_m$. A sharp peak would indicate a narrow range of $t_m$ that satisfies the observations (to a given level of statistical accuracy), and hence relatively low uncertainty in $t_m$. Conversely, a broader peak would indicate a wider range of $t_m$ that satisfies the observations (to the given level of statistical accuracy), and hence relatively large uncertainty in $t_m$ Note that the implementations discussed above are not intended to be exhaustive, but merely represent examples of potential variations. Furthermore, it will be appreciated that one or more of these potential variations may be combined as appropriate, depending upon the particular circumstances of any given implementation.

Testing

A test-retest dataset was utilised comprising 25 glaucoma patients (50 eyes), each of whom was subject to 10 Humphrey Visual Field Analyser (HFA) 24-2 visual field tests within 8 weeks. It is assumed that there is no measurable change during the 8-week period of time so the difference among the measurements from the same eye is due to the measurement variability. For the purpose of simulation, the average of the 10 visual fields is considered to be the underlying true visual field. The T4 test was configured to simulate such a 24-2 HFA visual field test. In particular, ten visual field tests were simulated with each true visual field using (i) the T4 test procedure, and (ii) the ZEST test procedure (zippy estimation by sequential testing) (King-Smith, 1994).

The patient response for stimulus at level s is simulated using a frequency of seen (FOS) curve parameterised as: FOS $(s,v,\delta)=1-FN(1-FN-FP)\phi(s|v,\delta)$, where FN is the false negative response rate, FP is the false positive response rate, and $\phi(s|v,\delta)$ is the cumulative normal distribution with mean v and standard deviation $\delta$. The mean v is the level of true differential light sensitivity (DLS) and $\delta$ is set as $\min[\exp(-0.081*v+3.27), 6]$ in order to reflect the increasing variability at higher level of DLS. The response is randomly generated with a positive response probability calculated as above.

Figure 5A:
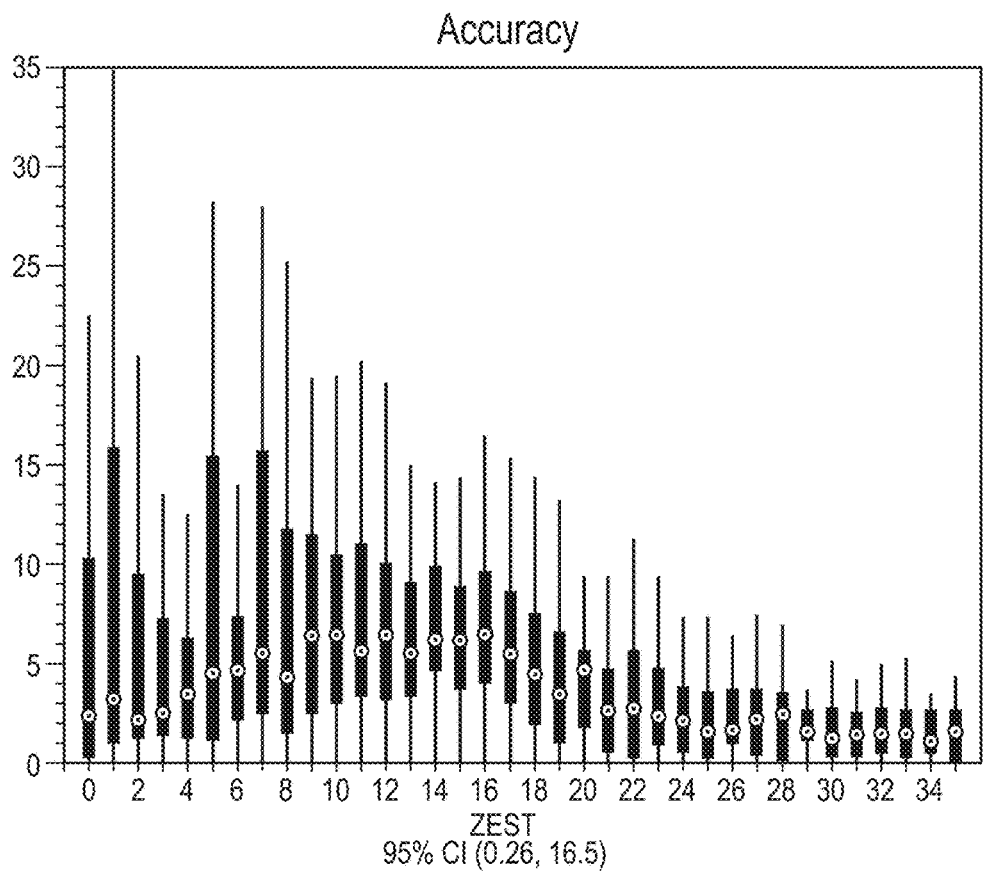
FIGS. 5A and 5B are plots from simulations comparing the performance of the test approach described herein (T4) against an existing test approach (ZEST), respectively showing accuracy and variability.
Figure 5A:
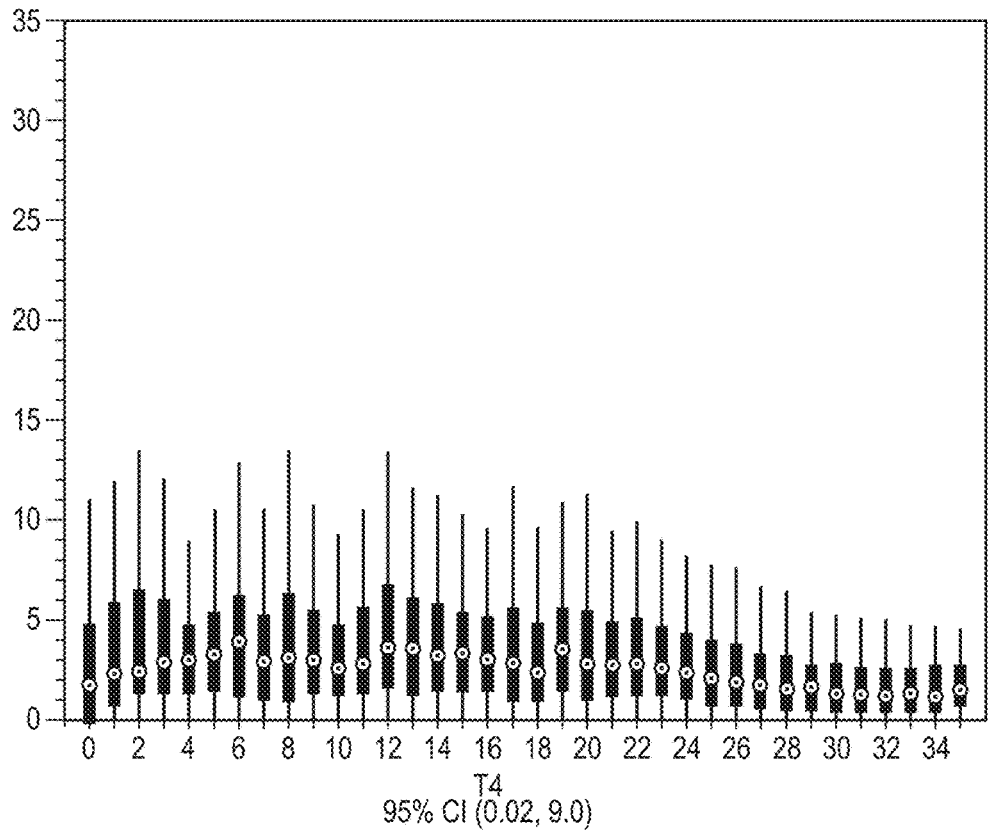
Figure 5B:
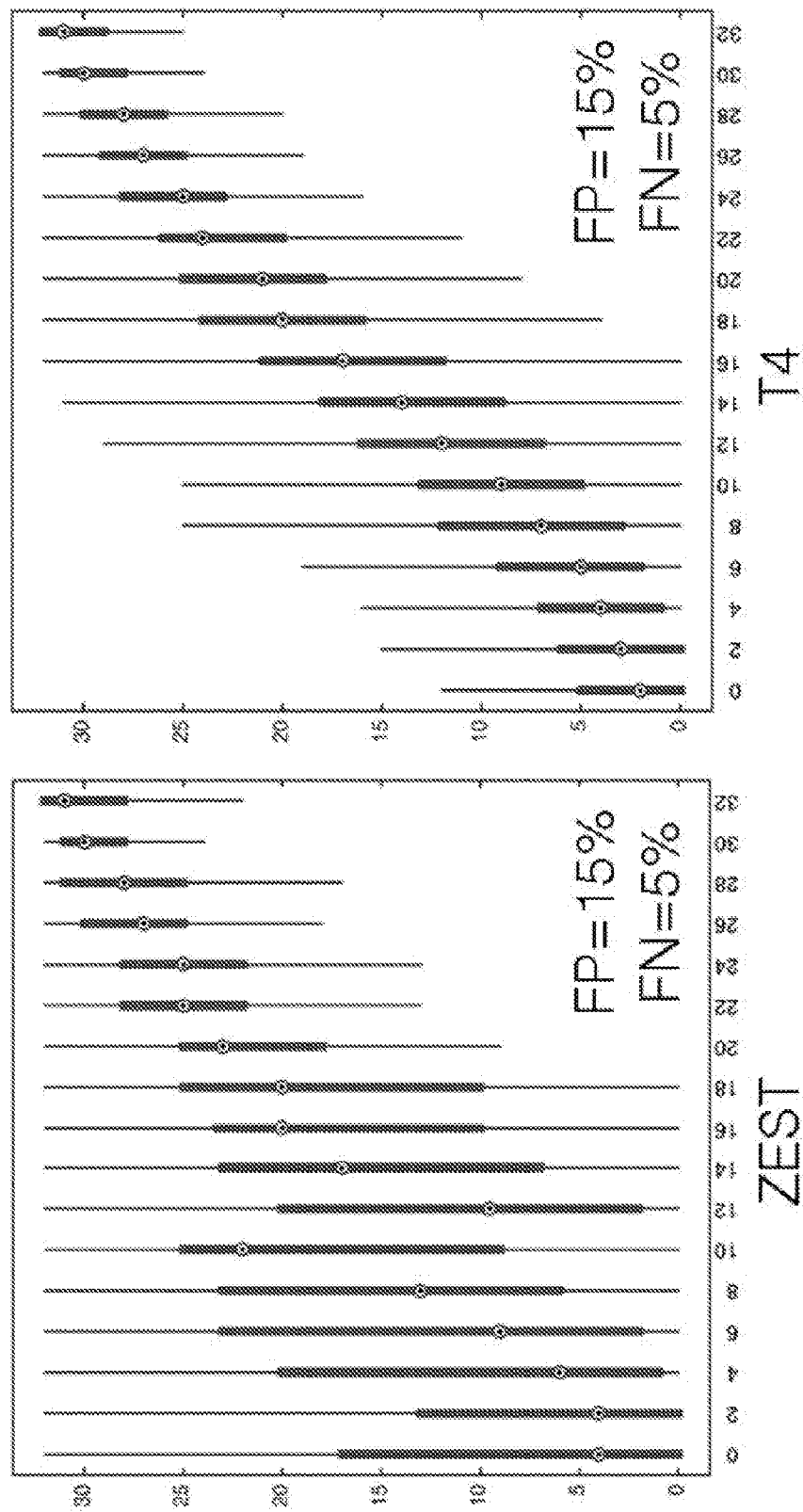

The T4 and ZEST test procedures were compared based on their accuracy and measurement variability. The accuracy is quantified as the absolute difference between the true and simulated visual field, while measurement variability is the difference between pairs of simulated visual fields of the same eye. Both accuracy and variability are stratified at different levels of DLS. The simulation results are shown in the plots of FIGS. 5A and 5B respectively.

In these diagrams, the x-axis represents the true sensitivity value (DLS) in dB (comparable with FIGS. 2A, 2B and 3A), while the y-axis represents the accuracy (difference between the true and simulated visual field) or variation (difference between different simulated values) found for that DLS value. In particular, for each DLS value, the light line represents the full range of differences found in the simulation, the heavier line represents the 95% range of differences found in the simulation, and the circle represents represent the average difference found in the simulation (for that DLS value). It can be seen that the results from the T4 procedure are generally more accurate (i.e. closer to the assumed true values) and with reduced variability (i.e. more consistent) than the results from the ZEST procedure.

Figure 6:
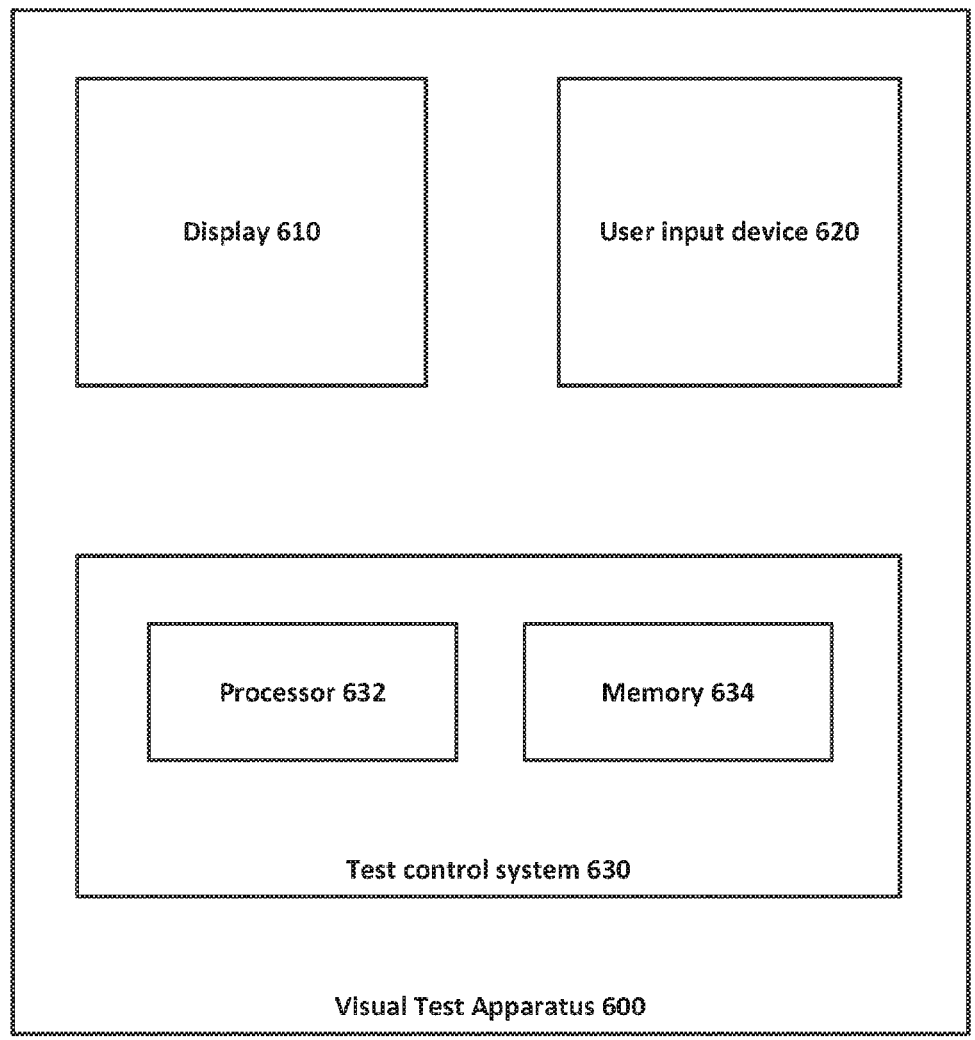
FIG. 6 is a schematic diagram illustrating an example apparatus for performing a visual test as described herein.

FIG. 6 is a schematic diagram illustrating an apparatus 600 for performing a visual test as described herein. The apparatus includes a display 610, e.g. a computer screen, on which to present the visual stimuli to a subject. Note that the display 610 may incorporate or be supplemented by a framework to help maintain the user's head (and eyes) in a fixed position relative to the screen; this in turn helps to ensure that a given display position on the screen coincides properly with a desired optical test location within the subject's visual field.

The apparatus 600 further includes a user input device 620 whereby the subject can indicate if the stimulus has been seen. Typically this user input device comprises a button which the subject presses if a stimulus is visible in order to give a positive response, while the response is negative if there is no such press of the button. However, other implementations could use a different form of user input, for example, an audio (spoken) input, touching or swiping a touch-screen, moving a joystick, etc.

The apparatus 600 further includes a test control system 630, which includes a processor 632 and a memory 534. The test control system manages the overall test procedure, determining which presentations to make to the subject on display 610 (as per the procedure described above), receiving the user input from device 620 indicating whether or not each presentation has been seen, and using the statistical model of Equation 7 to infer the visual sensitivity of the subject at each test location. The test control system 630 as shown in FIG. 6 may be implemented using a standard computer, although in other implementations the test control system 630 may comprise multiple such computers. Similarly, processor 632 may be implemented by multiple different processors (located in one or multiple machines). The memory 634 may include storage (such as a hard disk) for non-volatile storage of programs, data, etc, and also memory (typically volatile) for use at runtime, e.g. RAM, in order to support execution of such programs by processor 632.

The approach described above may be implemented using a computer program, which may be provided on a non-transitory computer readable storage medium, such as an optical disk (CD or DVD) or flash memory. The computer program may be loaded into the memory 634 from such a storage medium, or may be downloaded into the memory over a network, such as the Internet, for execution by the processor(s) 632 to perform the method described herein. In some cases the visual test apparatus may be implemented on a conventional general purpose computer running such a computer program; other implementations may use more specific hardware, e.g. an ASIC or GPU, such as for implementing the statistical model and performing the maximisations of Equation 7.

Although various implementations and embodiments have been described herein, it will be appreciated that these are presented by way of example only, and that various modifications and adaptions of such implementations will be apparent to the skilled person according to the circumstances of any given implementation. Accordingly, the present invention is not limited to the specific implementations and embodiments described herein, but rather is defined by the appended claims and their equivalents.

REFERENCES

Fitzke F W, Poinoosawmy D, Ernst W, Hitchings R A. Peripheral displacement thresholds in normals, ocular hypertensives and glaucoma, in *Perimetry Update* 1986/1987, E. Greve and A. Heijl, Editors, Kugler & Ghedini: The Hague, The Netherlands. 447-452.

Garway-Heath, D. F., J. Caprioli, et al. Scaling the hill of vision: the physiological relationship between light sensitivity and ganglion cell numbers. *Invest Ophthalmol Vis Sci.* 2000. 41 (7): 1774-82.

King-Smith, et al.: Efficient and Unbiased Modifications of the QUEST Threshold Method: Theory, Simulations, Experimental Evaluation and Practical Implementation. *Vision Res.* 34 (1994), 885-912. Verdon-Roe G M, Westcott M C, Viswanathan A C, Fitzke F W, Hitchings R A. Optimum number of stimulus oscillations for motion displacement detection in glaucoma, in *Perimetry Update* 2000/2001, M. Wall and J. Wild, Editors, Kugler Publications: The Hague, The Netherlands pp 97-102.

Verdon Roe G M, Development of a multi-location motion displacement test for detection of early glaucoma. Doctoral Thesis (2006a) *Institute of Ophthalmology, University College London.*

Verdon-Roe G M, Westcott M C, Viswanathan A C, Fitzke F W. Garway-Heath D F. Exploration of the psychophysics of a motion displacement hyperacuity stimulus. *Invest Ophthalmol Vis Sci.* 2006b. 47(11):4847-55.

What is claimed is:

1. A method for measuring a sensitivity level across a visual field of a subject defined by a set of locations using a visual test apparatus including a display, an input mechanism and a control system, said method comprising:

presenting by the control system a sequence of visual stimuli on the display, wherein each stimulus in the sequence has a respective intensity level and is positioned on the display to correspond to a respective location from the set of locations;

obtaining from the subject by the control system via the input mechanism, for each stimulus, a respective binary response indicating whether or not the stimulus was seen by the subject; and after receiving the response from the subject for a given stimulus in the sequence, using a statistical model in the control system to estimate, for each location in the set of locations, the sensitivity level at that location;

wherein:

the statistical model incorporates information about correlations in responses between different locations from the set of locations and takes, as input, the respective location, intensity level and response for multiple stimuli presented in said sequence up to and including the given stimulus;

the method is iterative in approach, and after receiving the response from the subject for each stimulus in the sequence, uses the statistical model in the control system to make a new estimate of the sensitivity level for each respective location in the set of locations;

wherein the new estimate takes, as input, the respective location, intensity level and response for multiple stimuli presented in said sequence up to and including the new stimulus, but not information derived therefrom; and the new estimate is derived using a maximisation algorithm, and an earlier estimate of sensitivity level derived earlier in the sequence is used only for initialization of the maximisation algorithm, whereby such initialization may assist the maximisation algorithm to converge more quickly, but does not impact the value of the newly estimated sensitivity level for each location.

2. The method of claim 1, further comprising, after receiving the response from the subject for a given stimulus in the sequence, the control system using the statistical model to estimate, for each location in the set of locations, the uncertainty in the estimated sensitivity level at that location.

3. The method of claim 1, further comprising, after estimating the sensitivity level of each location, determining whether to (i) present a further stimulus in said sequence, or (ii) terminate the sequence of presentations.

4. The method of claim 3, wherein termination of the sequence requires every location in the set of locations to have received a minimum number of stimulus presentations at the location.

5. The method of claim 4, wherein said minimum level is 2, 3 or 4.

6. The method of claim 3, wherein termination of the sequence requires the estimated uncertainty in the estimated sensitivity level at every location in the set of locations to be below a given threshold.

7. The method of claim 1, wherein the method comprises presenting stimuli and acquiring responses in a first portion of the sequence without estimating the sensitivity levels at the set of locations, prior to a second portion of the sequence in which the sensitivity levels at the set of locations are estimated after acquiring a new response to a presentation.

8. The method of claim 1, wherein the statistical model takes, as input, the respective location, intensity level and response for all stimuli presented in said sequence up to and including the given stimulus.

9. The method of claim 1, wherein the statistical model takes, as input, the respective location, intensity level and response for all stimuli presented in a most recent portion of the sequence.

10. The method of claim 1, wherein the statistical model takes, as input for estimating the sensitivity level at a given location, the respective location, intensity level and response for stimuli presented earlier in the sequence for which the correlation between the given location and the respective location is greater than a predetermined threshold.

11. The method of claim 1, wherein the correlation between a first location and a second location in the set of locations is calculated using a parameter based on the paths of optic nerve fibre bundles across the visual field that pass through or close to the first and second locations.

12. The method of claim 11, wherein the correlation is further based on the retinal distance between the first and second locations.

13. The method of claim 1, wherein using a statistical model in the control system to estimate, for each location in the set of locations, the sensitivity level at that location, is based on finding sensitivity levels for the locations that together maximise the likelihood of the responses for the multiple stimuli.

14. The method of claim 13, wherein the statistical model assumes that the responses are made in the presence of noise having a parameterised distribution, and estimating the sensitivity level at each location is based on finding sensitivity levels for the locations that together maximise the likelihood of the noise according to the parameterised distribution.

15. The method of claim 13, wherein using the statistical model to estimate the sensitivity levels provides a Bayesian approach.

16. The method of claim 15, wherein the sensitivity levels are assumed to have a prior comprising a normal distribution.

17. The method of claim 1, wherein said stimulus comprises performing a motion displacement test.

18. The method of claim 1, wherein the sensitivity is measured as part of a threshold test.

19. The method of claim 1, wherein the sensitivity is measured as part of a supra-threshold test, by estimating a sensitivity level that is above or below a threshold level by a given level of confidence.

20. A method for measuring a sensitivity level across a visual field of a subject defined by a set of locations using a visual test apparatus including a display, an input mechanism and a control system, said method comprising:

presenting by the control system a sequence of visual stimuli on the display, wherein each stimulus in the sequence has a respective intensity level and is positioned on the display to correspond to a particular location from the set of locations;

obtaining from the subject by the control system via the input mechanism, for each stimulus, a respective binary response indicating whether or not the stimulus was seen by the subject; and after receiving the response from the subject for a given stimulus in the sequence, using a statistical model in the control system to estimate, the sensitivity level at that location;

wherein:
the statistical model takes as input the respective intensity levels and responses for the stimuli presented in said sequence up to and including the given stimulus and uses a Bayesian approach to estimate the sensitivity level at that location by finding a sensitivity level that maximises the likelihood of the responses for the stimuli presented in said sequence;
the method is iterative in approach, and after receiving the response from the subject for each stimulus in the sequence, uses the statistical model in the control system to make a new estimate of the sensitivity level for each respective location in the set of locations;
wherein the new estimate takes, as input, the respective location, intensity level and response for multiple stimuli presented in said sequence up to and including the new stimulus, but not information derived therefrom; and
the new estimate is derived using a maximisation algorithm, and an earlier estimate of sensitivity level derived earlier in the sequence is used only for initialization of the maximisation algorithm, whereby such initialization may assist the maximisation algorithm to converge more quickly, but does not impact the value of the newly estimated sensitivity level for each location.

21. A non-transitory, computer-readable storage medium storing instructions that when executed by a computer cause the computer to perform a method for measuring a sensitivity level across a visual field of a subject defined by a set of locations using a visual test apparatus including a display, an input mechanism and a control system, said method comprising:
presenting by the control system a sequence of visual stimuli on the display, wherein each stimulus in the sequence has a respective intensity level and is positioned on the display to correspond to a particular location from the set of locations;
obtaining from the subject by the control system via the input mechanism, for each stimulus, a respective binary response indicating whether or not the stimulus was seen by the subject; and
after receiving the response from the subject for a given stimulus in the sequence, using a statistical model in the control system to estimate, the sensitivity level at that location;
wherein:
the statistical model takes as input the respective intensity levels and responses for the stimuli presented in said sequence up to and including the given stimulus and uses a Bayesian approach to estimate the sensitivity level at that location by finding a sensitivity level that maximises the likelihood of the responses for the stimuli presented in said sequence;
the method is iterative in approach, and after receiving the response from the subject for each stimulus in the sequence, uses the statistical model in the control system to make a new estimate of the sensitivity level for each respective location in the set of locations;
wherein the new estimate takes, as input, the respective location, intensity level and response for multiple stimuli presented in said sequence up to and including the new stimulus, but not information derived therefrom; and
the new estimate is derived using a maximisation algorithm, and an earlier estimate of sensitivity level derived earlier in the sequence is used only for initialization of the maximisation algorithm, whereby such initialization may assist the maximisation algorithm to converge more quickly, but does not impact the value of the newly estimated sensitivity level for each location.

22. An apparatus for measuring a sensitivity level across a visual field of a subject defined by a set of locations, the apparatus including a display, an input mechanism and a control system, said apparatus being configured to:
present by the control system a sequence of visual stimuli on the display, wherein each stimulus in the sequence has a respective intensity level and is positioned on the display to correspond to a respective location from the set of locations;
obtain from the subject by the control system via the input mechanism, for each stimulus, a respective binary response indicating whether or not the stimulus was seen by the subject; and
use, after receipt of the response from the subject for a given stimulus in the sequence, a statistical model in the control system to estimate, for each location in the set of locations, the sensitivity level at that location;
wherein:
the statistical model incorporates information about correlations in responses between different locations from the set of locations and takes, as input, the respective location, intensity level and response for multiple stimuli presented in said sequence up to and including the given stimulus;
the apparatus uses an iterative approach, and after receiving the response from the subject for each stimulus in the sequence, uses the statistical model in the control system to make a new estimate of the sensitivity level for each respective location in the set of locations;
wherein the new estimate takes, as input, the respective location, intensity level and response for multiple stimuli presented in said sequence up to and including the new stimulus, but not information derived therefrom; and
the new estimate is derived using a maximisation algorithm, and an earlier estimate of sensitivity level derived earlier in the sequence is used only for initialization of the maximisation algorithm, whereby such initialization may assist the maximisation algorithm to converge more quickly, but does not impact the value of the newly estimated sensitivity level for each location.

23. An apparatus for measuring a sensitivity level across a visual field of a subject defined by a set of locations, the apparatus including a display, an input mechanism and a control system, said apparatus being configured to:
present by the control system a sequence of visual stimuli on the display, wherein each stimulus in the sequence has a respective intensity level and is positioned on the display to correspond to a particular location from the set of locations;
obtain from the subject by the control system via the input mechanism, for each stimulus, a respective binary response indicating whether or not the stimulus was seen by the subject; and
use, after receipt of the response from the subject for a given stimulus in the sequence, a statistical model in the control system to estimate, the sensitivity level at that location;
wherein:
the statistical model takes as input the respective intensity levels and responses for the stimuli presented in said sequence up to and including the given stimulus and uses a Bayesian approach to estimate the sensitivity level at that location by finding a sensitivity level that maximises the likelihood of the responses for the stimuli presented in said sequence;

the apparatus uses an iterative approach, and after receiving the response from the subject for each stimulus in the sequence, uses the statistical model in the control system to make a new estimate of the sensitivity level for each respective location in the set of locations;

wherein the new estimate takes, as input, the respective location, intensity level and response for multiple stimuli presented in said sequence up to and including the new stimulus, but not information derived therefrom; and the new estimate is derived using a maximisation algorithm, and an earlier estimate of sensitivity level derived earlier in the sequence is used only for initialization of the maximisation algorithm, whereby such initialization may assist the maximisation algorithm to converge more quickly, but does not impact the value of the newly estimated sensitivity level for each location.

* * * * *